United States Patent [19]
Tsai

[11] Patent Number: 5,394,244
[45] Date of Patent: Feb. 28, 1995

[54] AMBIENT AIR REFRACTURE INDEX MEASURING DEVICE

[75] Inventor: John C. Tsai, Saratoga, Calif.

[73] Assignee: Excel Precision Inc., Santa Clara, Calif.

[21] Appl. No.: 957,597

[22] Filed: Oct. 6, 1992

[51] Int. Cl.⁶ .................................................. G01N 21/45
[52] U.S. Cl. ................................... 356/361; 356/130
[58] Field of Search ............... 356/361, 351, 358, 349, 356/130

[56] References Cited

U.S. PATENT DOCUMENTS

| | | | |
|---|---|---|---|
| 3,450,476 | 6/1969 | Rando | 356/361 |
| 4,733,967 | 3/1988 | Sommargren | 356/361 |
| 4,765,741 | 8/1988 | Detro et al. | 356/358 |
| 5,177,566 | 1/1993 | Leuchs et al. | 356/361 |

Primary Examiner—Vincent P. McGraw
Assistant Examiner—Peter J. Rashid
Attorney, Agent, or Firm—Michael J. Hughes

[57] ABSTRACT

An improved laser refractometer (10) employing a interferometer optical component (12), an object mirror (14) and an etalon (16). The etalon (16) is moved in the path of a plurality of reference beams (22, 24) and a plurality of measurement beams (26, 28) such that the reference beams (22, 24) travel through a vacuum within the etalon while the measurement beams (26, 28) travel a like distance through the etalon (16) in ambient air. In varying the distance traveled by the laser beams (22, 24, 26, 28) within the etalon (16) any interference fringes detected by an interference fringe detection device (20) are attributable to differences in the optical paths of the measurement beams (26, 28) as compared to that of the reference beams (22, 24) which, in turn, is entirely attributable to the ambient index of refraction. In a first preferred embodiment of the improved refractometer (10) the angular distance between a pair of plates (30, 32) is varied by rotation of the etalon (16). In an alternate embodiment of the etalon (516), the distance between plates (530, 532) is varied by linear displacement of the etalon (516).

19 Claims, 4 Drawing Sheets

AMBIENT AIR REFRACTURE INDEX MEASURING DEVICE

TECHNICAL FIELD

The present invention relates generally to the use of laser interferometers, and more particularly to an improvement which increases accuracy of measurement by providing for rapid and accurate compensation for changing refractive indices of the ambient air. The predominant current usage of the improved refractometer device and method of the present invention is in the precise measurement of relative movement, and thus of relative displacement, in scientific research and in applications requiring extreme measurement precision such as the manufacture of integrated circuits.

BACKGROUND ART

The development of the laser interferometer has provided an important advancement which has increased our ability to measure distances easily and precisely. The laser is no longer a laboratory curiosity. Rather, the laser interferometer is now a practical measuring tool for use in industrial environments. Currently, there are several various types of laser interferometer systems available, each utilizing some distinct properties of light and optics. However, regardless of which interferometric technique is used, when the measurement is to be conducted in an air environment, as is most practical in many applications, all such devices are limited by inaccuracies resulting from changes in the refractive index of the air through which the laser beams travel. This is due to the fact that laser wavelength in air is a function of the refractive index of the air, which in turn is dependent on pressure, humidity, temperature, gas content of the air, and the like. Variations in atmospheric conditions will change the value of the refractive index, thus affecting the measurement.

Because the measurements made by interferometric methods are substantially affected by the air refractive index, it is known in the art, when accurate measurements through air are required, to measure the air refractive index and to account therefor in analyzing the data obtained through interferometric measurements. Conventionally, the refractive index of air is determined using sensors to monitor the pressure, temperature and humidity of the ambient air, and the air refractive index is calculated based upon the results of such measurements. This calculation is commonly based upon an equation which was determined by one Edlen using data obtained empirically.

The above described conventional method for determining the air refractive index is quite adequate and useful for applications which do not approach the limits of accuracy of modern laser interferometers. However, cumulative errors in sensor data, and the fact that the empirically determined calculation is not exact, contribute to inaccuracies which may be quite significant in relation to precise measurements. Furthermore, this method does not take into account at all the fact that the ratio of the various species constituents of the air is not constant. Different gas species may have markedly different indexes of refraction. For example, carbon dioxide has a very high index of refraction, and so a small variation in carbon dioxide content in the air can considerably alter the wavelength readings of laser beams traveling through that air.

Yet another problem encountered using conventional methods for measuring the index of refraction of air is that there may be a significant time delay between the taking of readings and the calculated result. Therefore, the correction factor calculated by such means will lag behind the measurement data.

Clearly, a means for quickly and accurately determining the precise instantaneous index of refraction of the ambient air would be desirable. The present inventor has taught a means for using a laser interferometer to directly measure the index of refraction of air in a copending application Ser. No. 07/647,735. U.S. Pat. No. 4,847,512 issued to Seta teaches an application of a laser interferometer for indirectly measuring humidity (one of the factors affecting the index of refraction of air) by the method of using the interferometer to directly measure the index of refraction of the air. Of the means known to the inventor by which a laser interferometer might be utilized to measure the index of refraction of air, or a component thereof, while each is quite well suited to its intended purpose, none is readily adaptable to be used quickly and easily in conjunction with an interferometer, the primary purpose of which interferometer is to make some direct measurement not specifically related to the index of refraction measurement.

All of the prior art means for measuring the index of refraction of air known to the inventor have been less than sufficiently precise, or else they have been awkward and time consuming to use in practical field applications. To the inventor's knowledge, no prior art method for measuring the index of refraction of air has been readily adaptable for use with a conventional measurement interferometer without disrupting the normal usages of the interferometer or requiring that the interferometer be reconfigured to accomplish the measurement of the index of refraction.

DISCLOSURE OF INVENTION

Accordingly, it is an object of the present invention to provide a means to quickly and accurately measure the index of refraction of air in a laser interferometer measurement environment.

It is another object of the present invention to provide a means for measuring the index of refraction of air which does not require that the interferometer be moved or reconfigured to take the measurement.

It is a further object of the present invention to provide a means for measuring the index of refraction of the air in a laser interferometer environment which can be accomplished quickly, such that the measurement can be taken frequently in an industrial environment, wherein process speed is an important consideration.

It is yet another object of the present invention to provide a means for measuring the index of refraction of air which is relatively inexpensive to manufacture and to use.

It is still another object of the present invention to provide a means for measuring the index of refraction of air which is sufficiently rugged to withstand prolonged and repeated usages in an industrial environment.

Briefly, the preferred embodiment of the present invention is a refractometer having an etalon for placing in the path of laser interferometer measurement and reference beams. The etalon is devised such that moving the etalon keeps its effect on both the measurement beam and the reference beam equal, with the exception that the length of the path traveled through a vacuum by the reference beam is varied by a known amount.

Given that only the one variable is altered, any interference patterns produced by such movement may be attributed to that variation in the length of the path through vacuum, and it is a simple matter to quickly calculate the instant index of refraction of the surrounding air. The best presently known embodiment of the invention utilizes angular displacement of the etalon to vary the length of the laser beam path through vacuum. An equally preferred alternate embodiment of the invention utilizes linear displacement to achieve the same purpose. In the case of either embodiment of the invention presented herein, the etalon can be easily moved to take the desired air refractive index measurement without substantially interrupting the manufacturing process or other operation that is the primary purpose of the laser interferometer.

An advantage of the present invention is that the accuracy of laser interferometer distance measurements through air is improved.

Another advantage of the present invention is that it may be employed with existing laser interferometer measurement devices.

A further advantage of the present invention is that it the index of refraction of air may be quickly and accurately measured.

Yet another advantage of the present invention is that the measurement interferometer need not be reconfigured in order to measure the index of refraction of the ambient air.

Still another advantage of the present invention is that measurement of the index of refraction of air can be accomplished quickly, thus minimizing interference with the manufacturing process and, further, thus increasing the accuracy of measurement by minimizing time lag between the measurement of the index of refraction of air and an ensuing distance measurement.

Yet another advantage of the present invention is that it is relatively simple and inexpensive to manufacture.

Still another advantage of the present invention is that it is rugged and reliable in operation.

These and other objects and advantages of the present invention will become clear to those skilled in the art in view of the description of the best presently known modes of carrying out the invention and the industrial applicability of the preferred embodiments as described herein and as illustrated in the drawing.

BEST MODE FOR CARRYING OUT INVENTION

The best presently known mode for carrying out the invention is an improved refractometer device and method which is embodied to operate as a unit with existing laser interferometers. The predominant expected usage of the inventive improved refractometer device and method is in the microchip manufacturing industry, particularly in the control of wafer stepper apparatus wherein extremely high positioning accuracy is desirable and, further, wherein it is very undesirable to interrupt or to slow down the manufacturing process.

Figure 1:
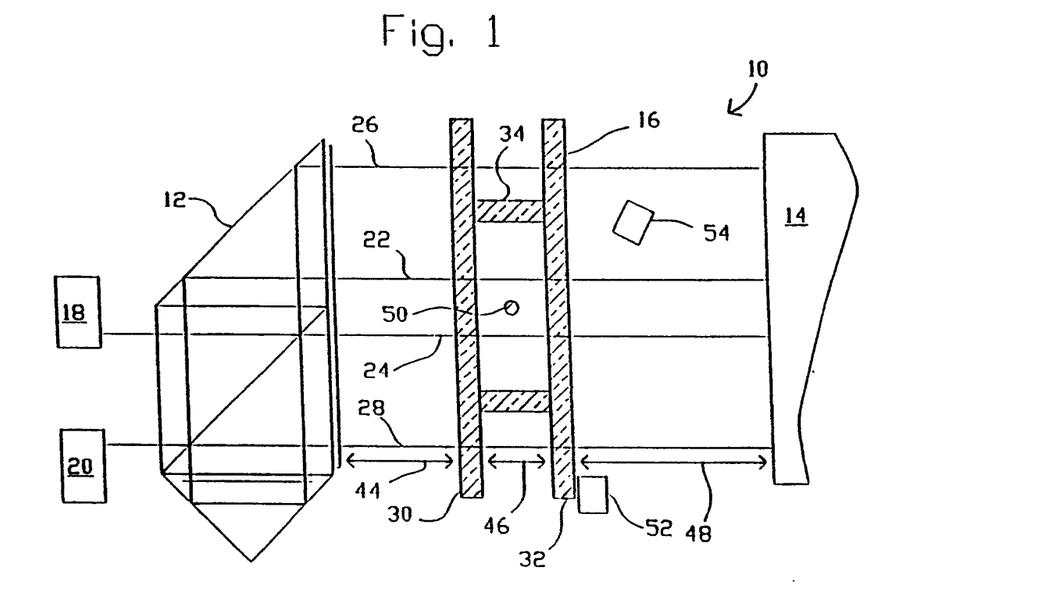
FIG. 1 is a two dimensional diagram of an improved refractometer according to the present invention.

The improved refractometer of the presently preferred embodiment of the present invention is illustrated in a side view two dimensional diagram in FIG. 1 and is designated therein by the general reference character 10. It should be noted that two dimensional diagrams such as FIG. 1 are commonly used in the field to depict optical paths. One skilled in the art will recognize that, although displacement between paths must be shown in such diagrams in the two available dimensions, such displacement may in fact occur in the third physical dimension in the actual embodiment of the device.

In many of its substantial components, the improved refractometer 10 does not differ significantly from conventional laser interferometric devices. Indeed, it is a feature of the best presently known embodiment 10 of the present invention that it works in conjunction with an existing interferometer optical component 12 and an object mirror 14. Both the interferometer optical component 12 and the object mirror 14 are employed primarily to accomplish a series of measurements not specifically associated with the present invention, and they also act in conjunction with an etalon 16 (shown in cross section in the view of FIG. 1) to form the present inventive improved refractometer 10. One skilled in the art will recognize that a laser emitting device 18 and a laser interference fringe detection device 20 are also required to perform measurements in conjunction with the interferometer optical component 12 and the object mirror 14.

The laser interferometer 12 of the best presently known embodiment 10 of the present invention is a "two pass" type, of which there are several variations available. One skilled in the art will recognize that the "two pass" interferometer 12 will have a first reference beam 22 and a second reference beam 24, each of which is directed from the interferometer optical component 12 toward the object mirror 14 and then reflected from the object mirror back toward the interferometer optical component 12. There are also a first measurement beam 26 and a second measurement beam 28, each of which is also directed from the interferometer optical component 12 toward the object mirror 14 and then reflected from the object mirror back toward the interferometer optical component 12. As can be seen in the view of FIG. 1, the etalon 16 is inserted in the path of both the reference beams 22 and 24 and the measurement beams 26 and 28. Although the best presently known embodiment 10 of the present invention utilizes a "two pass" interferometric technique, one skilled in the art could easily adapt the present invention for use with in single pass interferometers, or in interferometers having a greater number than two "passes".

Figure 2:
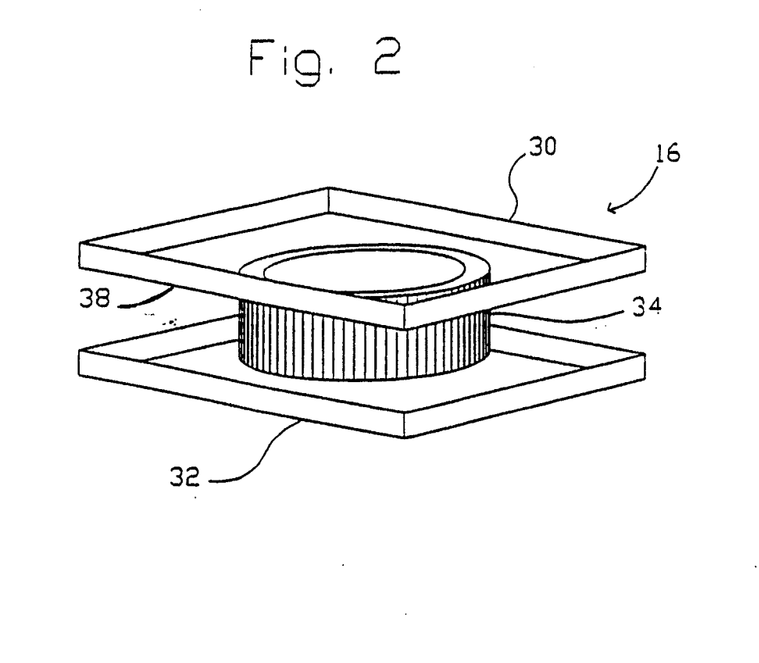
FIG. 2 is a perspective view of a first preferred embodiment of an etalon according to the present invention.
Figure 3:
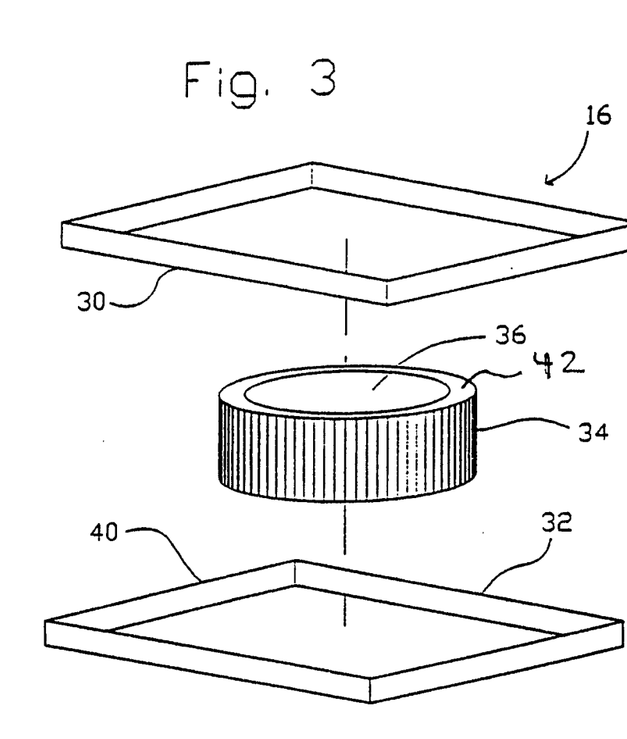
FIG. 3 is an exploded perspective view of the etalon of FIG. 2, rotated 180° as compared to the view of FIG. 2.

FIG. 2 is a perspective view of the etalon 16 of FIG. 1. As can be seen in the view of FIG. 2, the etalon 16 has a flat front plate 30, a flat back plate 32 and a tubular spacer 34. FIG. 3 is an exploded perspective view of the etalon 16 wherein it can be seen that the spacer 34 has a tubular passage 36 therethrough. The spacer 34, the front plate 30 and the back plate 32 of the best presently known embodiment 10 of the present invention are made of Zerodur TM, a commercially available ceramic, although any similar material with a low thermal expansion coefficient which is transparent to the laser wavelength could be used for the purpose. The etalon is assembled by a process known as optical contacting, which is merely the process of polishing a first planar surface 38 of the front plate 30, a second planar surface 40 (not visible in the view of FIG. 3) of the back plate 32 and a pair of opposing end surfaces 42 (only one of which is visible in the view of FIG. 3), which are those surfaces of the plates 30 and 32 and the spacer 34 which are to come into contact with each other, to be sufficiently smooth that they will have a cohesive attraction to each other. Furthermore, the tubular passage 36 of the etalon 16 is evacuated such that there is a relative vacuum therein, which also tends to hold the etalon 16 together. In order to accomplish this, the etalon 16 is assembled in a vacuum environment. Alternatively, the etalon could be assembled at atmospheric pressure with a valve (not shown) or other similar means provided such that the tubular passage 36 of the spacer 34 could be evacuated therethrough after the etalon 16 is assembled. The first planar surface 38 of the front plate 30 is parallel to the second planar surface 40 of the back plate 32 in the assembled etalon 16.

Referring again to FIG. 1, it can be seen that the etalon 16 is inserted into the path of the laser beams 22, 24, 26 and 28 such that the reference laser beams 22 and 24 travel through the evacuated tubular passage 36 in the spacer 34, while the measurement beams 26 and 28 are outside the spacer 34. All of the laser beams travel through both the front plate 30 and the back plate 32 of the etalon 16. As can be seen in the view of FIG. 1, each of the laser beams 22, 24, 26 and 28, as it travels between the interferometer optical component 12 and the object mirror 14, traverses a path that lies in part within the front plate 30 of the etalon 16 and, in part within the back plate 32, in part within a first laser path segment 44 lying between the interferometer optical component 12 and the front plate 30, in part within a second laser path segment 46 lying between the front plate 30 and the back plate 32, and in part within a third laser path segment 48 between the back plate 32 and the object mirror 14. As can be appreciated in light of the above discussion, then, all of the laser beams 22, 24, 26 and 28 travel like distance through the plates 30 and 32. Furthermore, all of the laser beams 22, 24, 26 and 28 travel a like distance through air except that, within the second laser path segment 46, the reference beams 22 and 24 are traveling through the evacuated tubular passage 36 of the etalon 16. Therefore, the cumulative paths of the reference beams 22 and 24 are optically identical to the cumulative paths of the measurement beams 26 and 28, with the single exception that the reference beams 22 and 24 travel less distance through air by the length of the second laser path segment 46.

Figure 4:
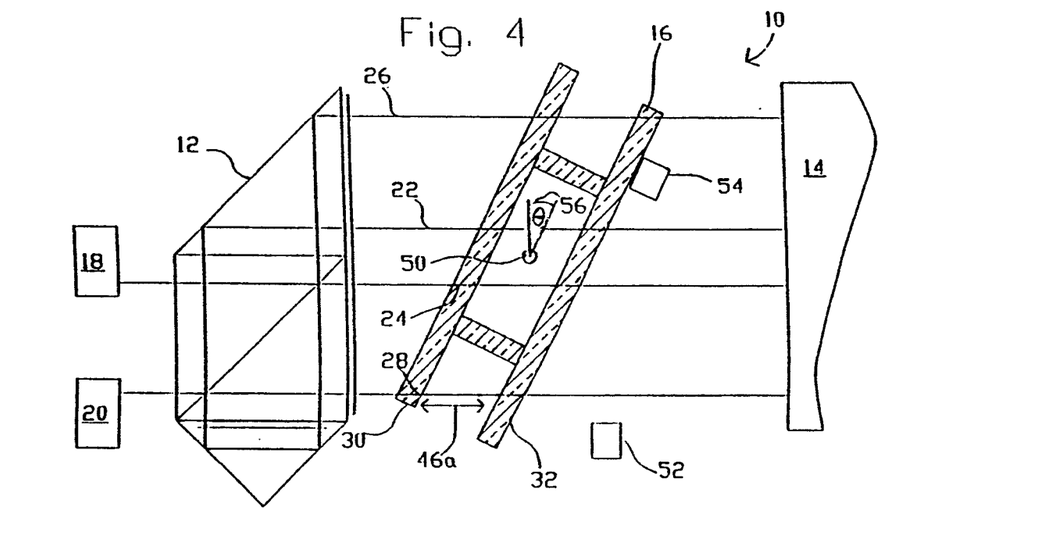
FIG. 4 is a two dimensional diagram of the improved refractometer of FIG. 1, showing the etalon rotated into a tilted position.

The etalon 16 is rotatably affixed within the best presently known embodiment 10 of the present invention such that it can be rotated about a pivot axis 50. In the view of FIG. 1, the etalon 16 is shown rotated such that it rests against a primary position stop 52. With the etalon 16 rotated against the primary position stop 52, the plates 32 and 32 of the etalon 16 are generally perpendicular to the laser beams 22, 24, 26 and 28. FIG. 4 is a diagrammatic view of the best presently known embodiment 10 of the present invention, similar to the view of FIG. 1, showing the etalon rotated about the pivot axis 50 such that it rests against a pivot position stop 54.

In the best presently known embodiment 10 of the present invention, the etalon 16 is rotated through a known angle ("$\phi$") 56 as it is pivoted fully about the pivot axis 50 between resting sequentially first against the primary position stop 52 and then against the pivot position stop 54. It should be noted that other, and perhaps more accurate means, for determining a precise amount of rotation of the etalon 16, instead of the mechanical stops 52 and 54. However, the inventor has found that the requisite amount of accuracy in attainment of the known angle 56 to maintain the overall accuracy of the inventive improved refractometer 10 (which will be discussed in more detail hereinafter) can be obtained using the mechanical stops 52 and 54.

As one skilled in the art of laser interferometry will know, changes in the length (either real or apparent) of the optical paths of the reference beams 22 and 24 and compared to the optical paths of the measurement beams 26 and 28 will produce interference fringes which can be detected and counted by the interference fringe detection device 20. The process of tilting the etalon 16 as described above will produce some effects which will not result in detectable fringes, such as the fact that the total length traveled by the laser beams 22, 24, 26 and 28 within the plates 30 and 32 will be changed by the act of rotating the etalon 16. However, since the reference beams 22 and 24 and the measurement beams 26 and 28 are affected equally, this will produce no interference pattern and this aspect of "change" in the configuration may be ignored for these present purposes. Indeed, the only significant change resulting from the described rotation of the etalon 16 will be that the length of the second laser beam segment 46 (FIG. 1) will increase as the etalon 16 is tilted away from its original position, generally perpendicular to the laser beams 22, 24, 26 and 28, such that the total distance which the reference beams 22 and 24 travel within the evacuated tubular passage 36 of the etalon 16 is increased. The increased length of the second laser beam segment 46 (FIG. 1) is designated in FIG. 4 by the reference character 46a Consequentially, the difference between the distances that the reference beams 22 and 24 travel through air, as compared to the distance that the measurement beams 26 and 28 travel through air is increased by a like amount.

We can, therefore, for these present purposes, examine just those portions of the laser beams 22, 24, 26 and 28 which lie between the plates 30 and 32, since any differences in the optical paths thereof will lie within that area. Given this limited scope of inquiry, the optical path for the reference beams 22 and 24 may be stated as:

$$m \cdot l \cdot (\sec\phi - 1)$$

where:
 $\phi$ is the angle of rotation of the etalon 16 (the known angle 56);
 m is the number of passes through the etalon 16 of the reference beams 22 and 24; and
 l is the length of the spacer 34.

The optical path of the measurement beams 26 and 28 may be stated as:

$$n \cdot m \cdot l(\sec\phi - 1)$$

where:

n is the index of refraction of the air during the measurement.

The relationship of the optical path of the measurement beams 26 and 28 to that of the reference beams 22 and 24 may be expressed as:

$$m \cdot (n-1) \cdot l \cdot (\sec\phi - 1) = N \cdot R$$

where:

N is the number of "counts" (the number of fringes counted by the interference fringe detection device 20); and R is the resolution of the counter (not shown) of the interference fringe detection device Since all of the other parameters in the immediately preceding equation are known, the value of n can easily be extracted. By feeding the findings of the interference fringe detector directly to a computer (not shown) the results of this calculation are, essentially, instantaneously available, and may be used in taking a primary measurement immediately after the inventive method is employed to determine the index of refraction of the ambient air. Indeed, the results of the air refraction measurement can be retained by the computer such that the computer can automatically apply a calculated "correction factor" to the subsequent primary measurement.

Using the above method, in an example where l=1.00 cm, m=2, $\phi=45°$, and the counter of the interference fringe detection device 20 has a resolution of 5.00 nm, the index of refraction can be measured to a value of $1.25 \cdot 10^{-7}$. The resolution of measurement can be further increased by either increasing the resolution of the electronic counter, or using multiple refractometer devices in series, as long as there is sufficient space between the interferometer optical component 12 and the object mirror 14 to permit this.

Figure 5:
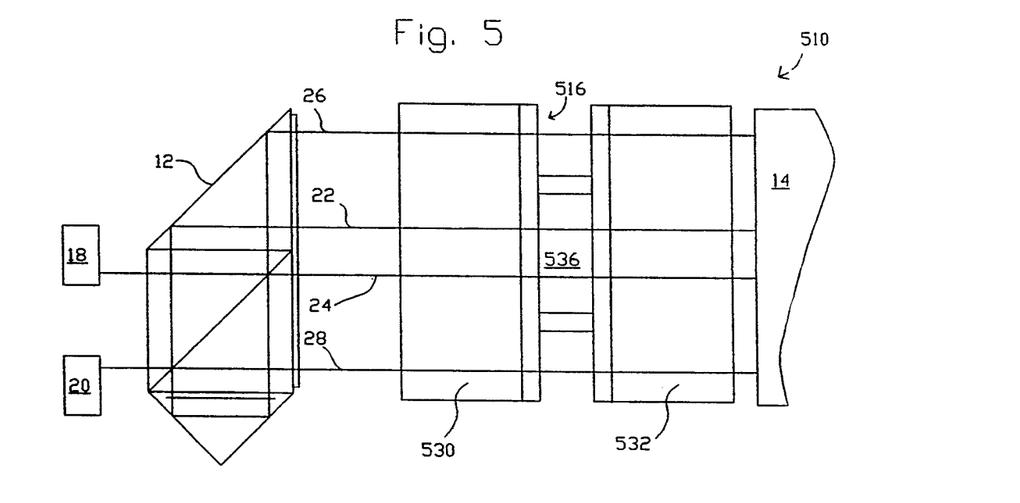
FIG. 5 is a diagrammatic side elevational view similar to the view of FIG. 1, showing an equally preferred alternate embodiment of the inventive improved refractometer.

FIG. 5 is a diagrammatic side elevational view, similar to the view of FIG. 1, showing an equally preferred alternative embodiment 510 of the present inventive improved refractometer. As can be seen in the view of FIG. 5, the laser emitting device 18, the interference fringe detection device 20, the interferometer optical component 12, the object mirror 14, and the laser beams 22, 24, 26 and 28 are all employed in the equally preferred alternative embodiment 510 of the invention substantially as they were in the first preferred embodiment 10 (FIG. 1) of the invention. However, in the equally preferred alternate embodiment 510 of the invention, an alternate etalon 516 is used instead of the etalon 16 of the first preferred embodiment 10.

Figure 6:
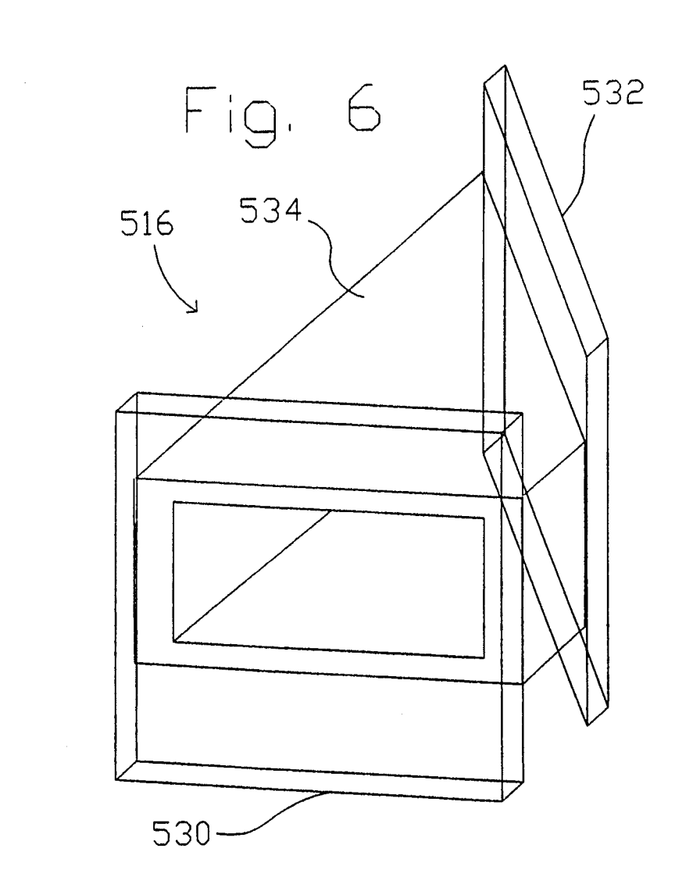
FIG. 6 is a perspective view of an alternate etalon for use in the improved refractometer of FIG. 5.
Figure 7:
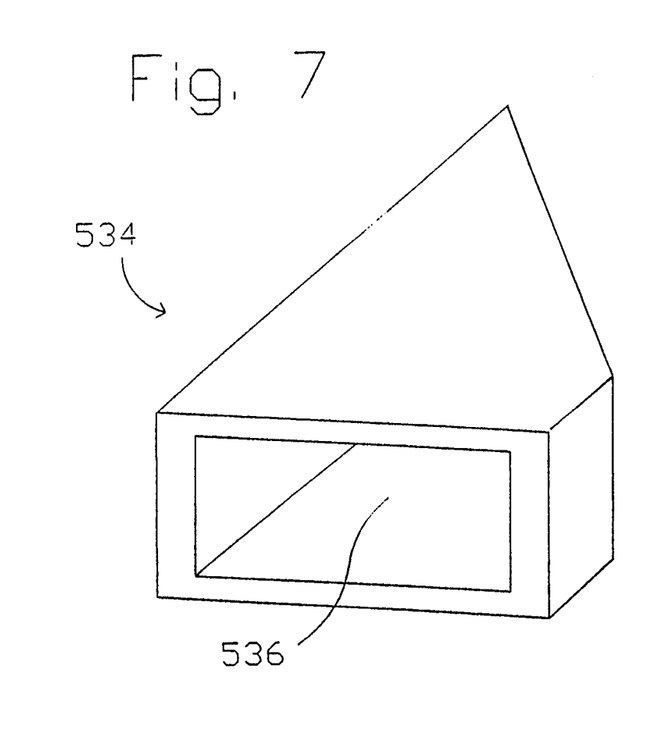
FIG. 7 is a perspective view of the alternate spacer of the alternate etalon of FIG. 6.

In FIG. 6 it can be seen that the alternate etalon 516 has an alternate front plate 530, an alternate back plate 532 and an alternate spacer 534. In FIG. 7 it can be seen that the alternate spacer 534 is a trapezoidal solid with having a generally rectangular passage 536 therethrough. The alternate etalon 516 is assembled in like manner to the etalon 16 to seal the ends of the rectangular passage 536 such that the rectangular passage 536 may have the air evacuated therefrom.

Figure 8:
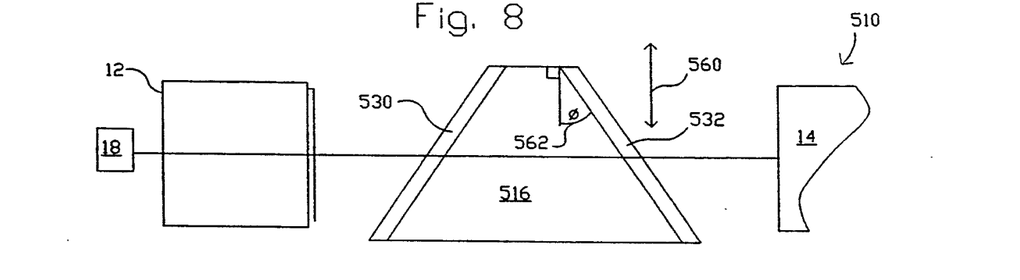
FIG. 8 is a top diagrammatic view of the improved refractometer of FIG. 5.

Referring again to FIG. 5, it can be seen that, in like manner to that employed with the etalon 16 in the first presently preferred embodiment 10 (FIG. 1) of the invention, the reference beams 22 and 24 travel through the evacuated rectangular passage 536 of the alternative etalon 516, while the measurement beams 26 and 28 do not. Therefore, as has been discussed heretofore in relation to the best presently known embodiment 10 (FIG. 1) of the present invention, the optical paths of the reference beams 22 and 24 differ from the optical paths of the measurement beams 26 and 28 in that the reference beams 22 and 24 travel the distance between 532 and 530 of the alternative etalon 534 in vacuum, while the measurement beams 26 and 28 travel that distance in air. FIG. 8 is a top diagrammatic view of the equally preferred alternate embodiment 510 of the present invention. An etalon movement plane 560 is indicated by a two headed arrow, indicating the plane along which the alternative etalon 516 is moved. From a comparison of the views of FIGS. 5 and 6 it can be appreciated that the orientation of the alternative etalon 516 depicted therein allows that all of the laser beams 22, 24, 26 and 28 (FIG. 5) travel like distances between the plates 530 and 532. Movement along the etalon movement plane 560 will result in a change in distances which the laser beams 22, 24, 26 and 28 travel between the plates 530 and 532. This is equivalent to the change produced by the tilting of the etalon 16, as has been previously discussed herein in relation to the first preferred embodiment 10 of the present invention. By moving the alternative etalon 516 between two predetermined points (not shown) along the etalon movement plane 560 the distance traveled by the laser beams 22, 24, 26 and 28 between the plates 530 and 532 is altered between two known values. The index of refraction of air is then determined according to the following calculation:

$$m \cdot (n-1) \cdot 2 \cdot y \cdot \tan(\phi/2) = N \cdot R$$

where:

$\phi$ is a half angle of the apex 562 of the trapezoidal etalon; and y is the displacement along the etalon movement plane 560.

With a 90° angle at the apex of the spacer 534 (that is, $\phi$ 562=45°), n=2, y=25 mm and 5 nm resolution for the electronics counter of the interference fringe detection device 20, a resolution of $5 \cdot 10^{-8}$ can be achieved. To further increase the resolution, the half angle of the apex 562 could be increased (as long as it is smaller than the Brewster angle), the resolution of the interference fringe detection device 20 could be increased, or multiple alternative etalons 516 could be used in series (space allowing).

As is shown above, in great part, the improved refractometers 10 and 510 according to the present invention closely resemble prior art conventional plane interferometer refractive index measuring devices. Among the substantial differences are the inventive etalons 16 and 516 which, when used in combination with the existing interferometer optical component 12 and the objective mirror 14 in the orientation and manner described herein provide for the quick and easy measurement of the ambient index of refraction without interference to the manufacturing process in which the invention is employed.

It should be noted that, in actual practice, the orientation of the improved refractometers 10 and 510 may vary from that shown in the above examples, because it is a feature of the present invention that the inventive etalons 16 and 516 be used in a variety of interferometer installations. One common example will be that, in practice, the objective mirror 14 will actually be two separate mirrors—a target mirror (not shown) from which the measurement beams 26 and 28 are reflected, and a reference mirror (not shown) from which the reference beams 22 and 24 are reflected. This variation will not affect the method or operation of the present invention.

Various other modifications may be made to the invention without altering its value or scope. For example, the inventive etalons 16 and 516 could be made in any of a variety of shapes and moved in any of a variety of planes or axis of rotation (or combinations thereof) such that the distance traveled by the reference beams 22 and 24 through vacuum varies along with a like distance traveled by the measurement beams 26 and 28 through the air (or other medium the index of refraction of which is to be measured), provided that such shape and movement keeps constant other variables (such as the relative lengths of laser beam paths and the distances traveled through glass or ceramic).

All of the above are only some of the examples of available embodiments of the present invention. Those skilled in the art will readily observe that numerous other modifications and alterations may be made without departing from the spirit and scope of the invention. Accordingly, the above disclosure is not intended as limiting and the appended claims are to be interpreted as encompassing the entire scope of the invention.

INDUSTRIAL APPLICABILITY

The laser interferometer is widely used in the field of metrology. The predominant current usages are for the measurement of very small distances, particularly in the production of microcircuit devices and in the field of scientific investigation. It is anticipated that the present invention will be widely accepted for use with existing and future laser interferometers because it provides an ideal solution to the problem that increasing needs for improved accuracy and resolution require that the index of refraction of the ambient air be known precisely while, on the other hand, it is very undesirable (particularly in the manufacturing environment) to slow down the measuring process by taking time to make the necessary measurements. Not only does the present invention improve the accuracy and repeatability of index of refraction measurements, it does so without the necessity of reconfiguring the laser interferometer or moving additional equipment into and out of place.

In practice, a measurement of the index of refraction of the ambient air may be taken as frequently as necessary in the extant conditions of usage. It should be noted that the ambient medium need not be air, and that any ambient medium which may be used in the interferometer environment (that is, a medium which is transparent to the laser beams used) could be measured according to the present invention.

Since the improved refractometers of the present invention may be readily constructed and incorporated into and as a part of prior art conventional laser interferometer systems it is expected that they will be acceptable in the industry as substitutes for the conventional index of refraction measuring means. For these and other reasons, it is expected that the utility and industrial applicability of the invention will be both significant in scope and long-lasting in duration.

I claim:

1. An improved refractometer comprising:
   a laser emitting device for emitting a first laser beam and a second laser beam;
   an object mirror;
   an interference fringe detector for detecting interference fringes caused by changes in the optical path of the first laser beam as compared to the optical path of the second laser beam;
   an interferometer optical component for separating the first laser beam from the second laser beam, and further for directing both of the laser beams toward said object mirror, and further for directing the laser beams from said object mirror into said interference fringe detector; and
   an etalon inserted in the path of the laser beams between said interferometer optical component and said object mirror such that the first laser beam passes through an enclosed evacuated passage in said etalon and the second laser beam passes through said etalon and outside the enclosed evacuated passage; wherein
   said etalon is movably mounted in relation to the laser beams such that the length of the path through the enclosed evacuated passage is variable according to the position of said etalon.

2. The improved refractometer of claim 1, wherein:
   the evacuated passage is enclosed by a generally tubular portion of said etalon, a first etalon end cap plate and a second etalon end cap plate, the first etalon end cap plate and the second etalon end cap plate being generally parallel to each other;
   said etalon is positioned in the path of the laser beams such that the first laser beam passes through the first end cap plate, the evacuated passage, and the second end cap plate;
   said etalon is further positioned in the path of the laser beams such that the second laser beam passes through the first end cap plate and the second end cap plate without passing through the evacuated passage; and
   said etalon is rotatably mounted in relation to the laser beams such that a portion of the paths of the laser beams between the first end cap plate and the second end cap plate is variable by the action of rotating said etalon.

3. The improved refractometer of claim 2, wherein:
   the generally tubular portion of said etalon is cylindrical in shape.

4. The improved refractometer of claim 2, and further including:
   a first physical stop for stopping rotation of said etalon in a first position wherein the path of the laser beams is generally perpendicular to the first end cap plate and the second end cap plate; and
   a second physical stop for stopping rotation of said etalon at a predetermined angle relative to the first position.

5. The improved refractometer of claim 1, wherein:
   said interferometer optical component is of a dual pass type such that the first laser beam passes four times through the evacuated chamber.

6. The improved refractometer of claim 1, wherein:
   the evacuated passage is enclosed by a generally tubular portion of said etalon, a first etalon end cap plate and a second etalon end cap plate, the generally tubular portion being asymmetrical such that the first etalon end cap plate and the second etalon end cap plate are not parallel to each other;

said etalon is positioned in the path of the laser beams such that the first laser beam passes through the first end cap plate, the evacuated passage, and the second end cap plate;

said etalon is further positioned in the path of the laser beams such that the second laser beam passes through the first end cap plate and the second end cap plate without passing through the evacuated passage; and said etalon is movably mounted in relation to the laser beams such that a portion of the paths of the laser beams between the first end cap plate and the second end cap plate is variable by the action of moving said etalon.

7. The improved refractometer of claim 6, wherein:

said etalon is generally trapezoidal in one aspect such that the first end cap plate and the second end cap plate form the non-parallel sides of the trapezoid.

8. The improved refractometer of claim 1, wherein:

at least those portions of said etalon through which the laser beams pass are made of a ceramic material.

9. A method for measuring the ambient refractive index using a laser interferometer, the laser interferometer having a first laser beam and a second laser beam which are directed at a target mirror and then compared to detect changes in the optical paths of the laser beams, the method comprising:

placing an etalon in the path of the laser beams such that the first laser beam and the second laser beam both travel through the etalon and further such that the first laser beam travels a known distance through an evacuated chamber of the etalon while the second laser beam travels a like distance through the etalon outside the evacuated chamber;

moving said etalon such that the known distance through the evacuated chamber is changed by a known amount;

counting fringes produced by moving said etalon.

10. The method of claim 9, and further including:

calculating the ambient refractive index by attributing all fringes counted to a difference in distance traveled by the second laser beam through air as compared to distance traveled by the first laser beam through air, such difference in distance being equal to the change in distance through the evacuated chamber caused by the movement of said etalon.

11. The method of claim 10, and further including:

using the calculated ambient refractive index as a correction factor in taking subsequent measurements.

12. The method of claim 9, wherein:

the evacuated chamber of said etalon is partially defined by a first plate and a second plate, the first plate and the second plate being parallel where the laser beams pass therethrough such that the first laser beam and the second laser beam travel like distances through and between the first plate and the second plate; and said etalon is rotatably mounted in relation to the laser beams such that the distance traveled by the laser beams between the first plate and the second plate can be altered by rotating said etalon.

13. The method of claim 9, wherein:

the evacuated chamber of said etalon is partially defined by a first plate and a second plate, the first plate and the second plate being skewed such that moving said etalon in relation to the laser beams alters the distance which the laser beams travel between the first plate and the second plate.

14. The method of claim 9, wherein:

the laser interferometer is of a multiple pass type such that the first laser beam and the second laser beam each traverse the etalon in a like number of multiple passes.

15. A refractometer for determining the refractive index of ambient air, including:

a laser interferometer having a laser emitting means for emitting a first laser beam and a second laser beam, an interferometer optical component for directing the first laser beam and the second laser beam to a target mirror and then into a fringe detection apparatus; and an etalon movably mounted between the laser emitting means and the target mirror such that the length of the paths of the laser beams through said etalon are variable by moving said etalon; wherein said etalon includes a first plate and a second plate defining the length of the paths of the laser beams through said etalon;

the first laser beam and the second laser beam travel like distances between the first plate and the second plate; and the first laser beam travels through vacuum between the first plate and the second plate while the second laser beam travels through the ambient air between the first plate and the second plate.

16. The refractometer of claim 15, wherein:

said etalon is formed and positioned such that moving said etalon alters the length of the path of the first laser beam through the ambient air between the laser emitting means and the target mirror as compared to the path of the path of the second laser beam through the ambient air between the laser emitting means and the target mirror.

17. The refractometer of claim 15, wherein:

the first plate and the second plate are parallel; and the length of the paths of the first laser beam and the second laser beam between the first plate and the second plate is varied by rotating said etalon.

18. The refractometer of claim 15, wherein:

the first plate and the second plate are not parallel such that the length of the paths of the first laser beam and the second laser beam between the first plate and the second plate is varied by moving said etalon across the paths of the laser beams.

19. The refractometer of claim 15, wherein:

fringes detected at the fringe detection apparatus are a function of the ambient refractive index and the variation of the length of the path of the first laser beam through vacuum.

* * * * *